(12) United States Patent
Eisenstark et al.

(10) Patent No.: US 8,282,919 B2
(45) Date of Patent: Oct. 9, 2012

(54) **MICROORGANISM STRAIN CRC2631 OF *SALMONELLA TYPHIMURIUM* AND ITS USE AS A CANCER THERAPEUTIC**

(75) Inventors: Abraham Eisenstark, Columbia, MO (US); Robert A. Kazmierczak, Columbia, MO (US)

(73) Assignee: Cancer Research Center, Columbia, MO (US)

( * ) Notice: Subject to any disclaimer, the term of this patent is extended or adjusted under 35 U.S.C. 154(b) by 437 days.

(21) Appl. No.: 12/472,254

(22) Filed: May 26, 2009

(65) Prior Publication Data
US 2010/0135973 A1 Jun. 3, 2010

Related U.S. Application Data

(60) Provisional application No. 61/055,848, filed on May 23, 2008.

(51) Int. Cl.
*A01N 63/00* (2006.01)
*C12N 1/20* (2006.01)
*C12Q 1/02* (2006.01)

(52) U.S. Cl. .............. 424/93.48; 435/252.8; 435/29

(58) Field of Classification Search .......... 424/93.48; 435/252.8, 29
See application file for complete search history.

(56) References Cited

U.S. PATENT DOCUMENTS
5,110,588 A * 5/1992 Morona et al. ............ 424/200.1

OTHER PUBLICATIONS http://www.cancerresearchcenter.org. (Prostate Tumor Targeting and Killing Mechanisms by *Salmonella typhimurium* in the Mouse Model. Aug. 27, 2007).*
Stocker et al. (*Salmonella typhimurium* Mutants of RfaH- Phenotype: Genetics and Antibiotic Sensitivities. Journal of General Microbiology. 1980. 116: 17-24).*
Nagy et al. (Oral Immunization with an rfaH Mutant Elicits Protection against Salmonellosis in Mice. Infect. Immun. 2004. 72(7): 4297).*
Brown et al. (An Attenuated aroA *Salmonella typhimurium* Vaccine Elicits Humoral and Cellular Immunity to Cloned Beta-Galactosidase in Mice. 1987. Journal of Infection Diseases 155:86-92).*
Abraham Eisenstark, et al.; Development of *Salmonella* Strains as Cancer Therapy Agents and Testing in Tumor Cell Lines; Methods in Molecular Biology, vol. 394: *Salmonella*: Methods and Protocols, edited by H. Schatten and A. Eisenstark, Humana Press Inc., Totowa, NJ, 2007.
Zhisheng Zhong, et al.; *Salmonella*—Host Cell Interactions, Changes in Host Cell Architecture, and Destruction of Prostate Tumor Cells with Genetically Altered *Salmonella*; Microscopy & Microanalysis, Microscopy Society of America 13, 372-383, 2007.

* cited by examiner

*Primary Examiner* — Karen Cochrane Carlson
*Assistant Examiner* — Natalie Moss
(74) *Attorney, Agent, or Firm* — Spencer Fane Britt & Browne LLP (57) ABSTRACT

The present invention provides a biologically pure isolate of the genus *Salmonella* having a disruption of at least one gene selected from the group consisting of aroA, rfaH, and thyA, as well as a method of treating cancer including the step of administering such a *Salmonella* to a subject in need thereof.

4 Claims, 6 Drawing Sheets

SEQUENCE LISTING

```
<160> NUMBER OF SEQ ID NOS: 4

<210> SEQ ID NO 1
<211> LENGTH: 59
<212> TYPE: DNA
<213> ORGANISM: Artificial Sequence
<220> FEATURE:
<223> OTHER INFORMATION: Primer sequence complementary to portion of
      thyA gene of S. typhimurium.

<400> SEQUENCE: 1
ttagatagcg accggcgctt taataccggg gtgcggatcg tgtaggctgg agctgcttc      59

<210> SEQ ID NO 2
<211> LENGTH: 59
<212> TYPE: DNA
<213> ORGANISM: Artificial Sequence
<220> FEATURE:
<223> OTHER INFORMATION: Primer sequence complementary to a portion of
      the thyA gene of S. typhimurium.

<400> SEQUENCE: 2
atgaaacagt atttagaact gatgcaaaaa gtgctggatc atatgaatat cctccttag      59

<210> SEQ ID NO 3
<211> LENGTH: 59
<212> TYPE: DNA
<213> ORGANISM: Artificial Sequence
<220> FEATURE:
<223> OTHER INFORMATION: Primer sequence complementary to a portion of
      the sequence of rfaH of S. typhimurium.
```

```
<400> SEQUENCE: 3
ctaaatcttg cgaaaaccgg tgttttttac gctctgcttg tgtaggctgg agctgcttc        59

<210> SEQ ID NO 4
<211> LENGTH: 59
<212> TYPE: DNA
<213> ORGANISM: Artificial Sequence
<220> FEATURE:
<223> OTHER INFORMATION: Primer sequence complementary to a portion of
      the rfaH sequence of S. typhimurium.

<400> SEQUENCE: 4
atgcaatcct ggtatttact gtactgcaaa cgcgggcaac atatgaatat cctccttag        59
```

MICROORGANISM STRAIN CRC2631 OF SALMONELLA TYPHIMURIUM AND ITS USE AS A CANCER THERAPEUTIC

RELATED APPLICATIONS

This application claims priority of U.S. Provisional Patent Application No. 61/055,848, filed May 23, 2008 and incorporated herein by reference in its entirety.

INCORPORATION-BY-REFERENCE OF SEQUENCE LISTING

The Sequence Listing, which is a part of the present disclosure, includes a text file "CRC_ST25.txt," generated by U.S. Patent & Trademark Office Patent In Version 3.5 software, comprising nucleotide sequences of the present invention. This .txt file has been filed electronically herewith and is incorporated herein by reference in its entirety.

BACKGROUND OF THE INVENTION

1. Field of the Invention

The present invention relates generally to a novel microorganism strain, *Salmonella typhimurium* CRC2631, and it use as a cancer therapeutic.

2. Description of the Prior Art

The term 'cancer' refers generally to a condition in which cells in an organism undergo unchecked growth, tending toward limitless expansion and creation of a tumor. Cancer can originate anywhere in the human body. Cancers that arise from cells covering internal and external body surfaces are referred to as 'carcinomas,' while those developing from cells comprising the body's supportive tissues (such as fat, cartilage, bone, and the like) are called 'sarcomas.' Other categories of cancers include lymphomas and leukemias.

The unregulated growth of cancer cells is typically due to a mutation in the DNA of the cell, such as, for example, in genes controlling cell growth (e.g. the transformation of proto-oncogenes into oncogenes). In early stages, such mutations are not noticeable, and a cancer is typically discovered only after it has grown severe enough to produce symptoms in the patient. Early screening techniques can detect cancers prior to the onset of noticeable symptoms in the patient. Breast cancer, for example, is detectable in early stages by the use of mammography. Testing PSA levels in males, coupled with direct rectal exams, can allow a physician to detect early stages of prostate cancer. Early detection of a cancer significantly increases the likelihood of successful treatment of the patient.

A variety of treatment options exist for the cancer patient. For a male suffering from prostate cancer, for example, hormone-ablative therapy is often effective in treating the early stages of the disease. If the cancer progresses to an androgen-independent stage, other chemotherapies, such as the use of the compound taxol, are indicated. Patients can, however, develop resistance to chemotherapeutic agents such as taxol, and many chemotherapeutic agents are highly toxic to the body. Thus, alternative therapies are desired.

*Salmonella* is a genus of gram-negative, rod-shaped enterobacteria. The genus contains over 2,000 sero-species and is one of the most important pathogens in the Enterobacteriaceae family. They are facultative anaerobes, non-spore forming, and are usually motile, having peritrichous flagella. The organisms use citrate as a sole carbon source and typically ferment glucose, but not sucrose or lactose.

Taxonomically, all *Salmonella* fall into two species: *S. enterica*, and *S. bongori*, with six subspecies present. Popular species names, based largely on sero-typing, are commonly used. *Salmonella* are often referred to by genus and serovar, such as *S. typhimurium*, rather than by an extended nomenclature such as *S. enterica* subspecies *enterica* serovar *typhimurium*. For purposes of this document, the name *S. typhimurium* will be used to refer to *S. enterica* subspecies *enterica* serovar *typhimurium*.

*S. typhimurium* is among the more common of the *Salmonella* serovars. The organism has a circular chromosome of approximately 4,857 kilobases (kb). It is known to cause salmonellosis in humans with varying degrees of severity. In some cases hospitalization is required. Clinical isolation of *S. typhimurium* is typically performed using MacConkey, XLD, XLT, DCA, or Önöz agars. Preliminary isolation generally requires a selective medium because of the presence of normal intestinal flora in the sample.

*Salmonella*-based therapies have been described with respect to prostate and breast cancers. *Salmonella typhimurium* strains, for example, have been found to target and destroy breast cancer and prostate cancer cells both in vitro and in animal models. *S. typhimurium* strain VNP20009, a *Salmonella* derived from strain ATCC14028, has been used in Phase I clinical trials for treatment of human cancers, but was found to have unacceptable levels of toxicity and was therefore unacceptable for use as a therapeutic organism.

What is needed, then, is a strain of *S. typhimurium* having reduced or no toxicity while retaining the ability to target and destroy cancer cells.

SUMMARY OF THE INVENTION

The present invention provides novel strains of the bacterium *Salmonella typhimurium* for use as a cancer therapeutic.

One aspect of the present invention provides a biologically pure isolate of the genus *Salmonella* having a disruption of at least one gene selected from the group consisting of aroA, rfaH, and thyA.

Another aspect of the present invention provides a biologically pure isolate of the genus *Salmonella* having a disruption of each of the genes aroA, rfaH, and thyA.

Another aspect of the present invention provides a biologically pure isolate of *Salmonella typhimurium* strain CRC2631.

Still another aspect of the present invention provides a biologically pure isolate of *Salmonella typhimurium* strain CRC2636.

Another aspect of the invention provides a method of treating cancer, the method including the step of administering to a subject a therapeutically effective amount of *Salmonella* having a disruption of at least one gene selected from the group consisting of aroA, rfaH, and thyA.

In another aspect of the present invention, the method of treating cancer includes administering to a subject a therapeutically effective amount of *Salmonella* having a disruption of each of the genes aroA, rfaH, and thyA.

In still another aspect of the present invention, the method of treating cancer includes administering to a subject a therapeutically effective amount of *Salmonella typhimurium* strain CRC2631.

In still another aspect of the present invention, the method of treating cancer includes administering to a subject a therapeutically effective amount of *Salmonella typhimurium* strain CRC2636.

In another aspect of the present invention, the subject being treated by the present methods is a human. In another aspect of the present invention, the cancer being treated by the present methods is prostate cancer.

In still another aspect of the invention, a method for treating cancer is provided, the method including the step of administering to a subject in need thereof a therapeutic agent bound to *Salmonella* having a disruption of at least one gene selected from the group consisting of aroA, rfaH, and thyA.

In another aspect of the invention, a method for treating cancer is provided, the method including the step of administering to a subject in need thereof a therapeutic agent bound to *Salmonella* having a disruption of each of aroA, rfaH, and thyA.

In still another aspect of the invention, a method for treating cancer is provided, the method including the step of administering to a subject in need thereof a therapeutic agent bound to a molecule capable of binding mannose-linked GlcNAcβ1-4GlcNAcβ-N/Gly, mannose-linked Manα1-6Manα-Sp9, or transferring-lined glycans.

DETAILED DESCRIPTION OF THE PREFERRED EMBODIMENTS

Definitions

"Agent" or "Therapeutic Agent:" As used herein, the terms "agent" and "therapeutic agent" refer to any natural or synthesized composition that when administered to a subject relieves the subject of disease or improves health. Wherein the disease being treated is cancer. The "agent" or "therapeutic agent" may be a pro-drug, further defined below.

"Bind, Binds, or Interacts With:" As used herein, "bind," "binds," or "interacts with" means that one molecule recognizes and adheres to a particular second molecule in a sample, in vitro or in vivo, but does not substantially recognize or adhere to other structurally-unrelated molecules in the sample. Generally, a first molecule that "specifically binds" a second molecule has a binding affinity of greater than about $10^5$ or $10^6$ moles/liter for that second molecule.

"Gene:" As used herein, the term "gene" means a nucleic acid molecule that codes for a particular protein, or in certain cases, a functional or structural RNA molecule.

"Labeled:" The term "labeled," with regard to a probe or antibody, is intended to encompass direct labeling of the probe or antibody by coupling (i.e., physically linking) a detectable substance to the probe or antibody.

"Native:" When referring to a nucleic acid molecule or polypeptide, the term "native" refers to a naturally-occurring (e.g., a "wild-type") nucleic acid or polypeptide.

"Nucleic Acid or Nucleic Acid Molecule:" As used herein, the term "nucleic acid" or "nucleic acid molecule" means a chain of two or more nucleotides such as RNA (ribonucleic acid) and DNA (deoxyribonucleic acid). A "purified" nucleic acid molecule is one that is substantially separated from other nucleic acid sequences in a cell or organism in which the nucleic acid naturally occurs (e.g., 30%, 40%, 50%, 60%, 70%, 80%, 90%, 95%, 96%, 97%, 98%, 99%, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

"Pharmaceutically Acceptable:" As used herein, the term "pharmaceutically acceptable" means approved by a regulatory agency of the Federal or a state government or listed in the U.S. Pharmacopeia or other generally recognized pharmacopeia for use in animals, and more particularly in humans.

"Pharmaceutically Acceptable Carrier:" As used herein, the term "pharmaceutically acceptable carrier" refers to a diluent, adjuvant, excipient, or vehicle with which a composition is administered. Such carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when a composition is administered intravenously. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. A composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier.

"Pro-drug:" As used herein, the term "pro-drug" refers to any composition which releases an active drug in vivo when such a composition is administered to a mammalian subject. Pro-drugs can be prepared, for example, by functional group modification of a parent drug. The functional group may be cleaved in vivo to release the active parent drug compound. Pro-drugs include, for example, compounds in which a group that may be cleaved in vivo is attached to a hydroxy, amino or carboxyl group in the active drug. Examples of pro-drugs include, but are not limited to esters (e.g., acetate, methyl, ethyl, formate, and benzoate derivatives), carbamates, amides and ethers. Methods for synthesizing such pro-drugs are known to those of skill in the art.

"Subject:" As used herein, the terms "subject" and "subjects" refer to any mammal, including a human mammal.

Non-human animals subjects may include, but are not limited to, mammals such as primates, mice, pigs, cows, cats, goats, rabbits, rats, guinea pigs, hamsters, horses, sheep, dogs, and the like. Such animals may be companion animals, as in the case of dogs and cats, for example, or may be trained animals including therapy animals such as a therapy dog.

Also included are service animals, such as dogs that assist persons who are in need of assistance due to loss or impairment of sight, hearing, or other senses. Further, non-human subjects may include working animals such as dogs or other animals trained for security or rescue work. Also included are animals trained or maintained for procreation or entertainment purposes, including purebred animal breeds, racehorses, or workhorses. Animals that are genetically-engineered are likewise included, regardless of the purposes of the genetic engineering, as are rare or exotic animals, including zoo animals and wild animals.

"Therapeutically Effective Amount:" As used herein, the term "therapeutically effective amount" refers to those amounts that, when administered to a particular subject in view of the nature and severity of that subject's disease or condition will have a desired therapeutic effect, e.g. an amount that will cure, prevent, inhibit, or at least partially arrest or partially prevent a target disease or condition.

"G," "C," "A," "T" and "U" (irrespective of whether written in capital or small letters) each generally stand for a nucleotide that contains guanine, cytosine, adenine, thymine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, thymine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine.

In accordance with the present invention, there may be employed conventional techniques of molecular biology and microbiology. These techniques are within the skill in the art and are explained fully in the literature. See, for example, Sambrook, Fritsch & Maniatis, MOLECULAR CLONING: A LABORATORY MANUAL, Third Edition (2001), Cold Spring Harbor Laboratory Press, Cold Spring Harbor, N.Y.

The present invention is directed to a novel microorganism strain designated *Salmonella typhimurium* CRC2631 (*S. enterica* subspecies *enterica* serovar *typhimurium*), and its use as a cancer therapeutic. The strain has been derived from a *Salmonella typhimurium* LT2 hisD2550 mutant, CRC1674, as described below. The toxicity of the CRC2631 strain was attenuated by long-term archival storage as well as direct manipulation of the microorganism's genome.

Archival Storage of *Salmonella typhimurium* CRC1674

In April of 1967, an inoculum of *S. typhimurium* strain CRC1674 was placed in a sealed glass stab jar containing solid Luria-Bertani (LB) agar. A plug of this archival agar stab was extracted and grown in LB broth on Jan. 19, 1999, meaning that the *S. typhimurium* strain at issue was stored under archival conditions for approximately 32 years. A number of mutations in the microorganism were observed after the period of archival storage, and these mutations are described in the literature and known in the art. After storage, CRC1674 had developed, for example, a G168T mutation of rpoS (RNA-polymerase sigma factor). Further, the hisD2550 auxotrophic mutation in the parent strain was partially suppressed. Ten genes located in the membrane region of the microorganism were also deleted, and one-hundred eighty-two genes showed substantial changes (amounting to 4.4% of the genome).

Production of Strain CRC2631 from Archival CRC1674

Archival strain CRC1674 retains a level of toxicity that renders it undesirable for use in human cancer therapies. In order to reduce this toxicity to acceptable levels, the present invention was developed, and the process of that development is now described.

In order to reduce the toxicity of CRC1674, and thus produce the present invention, CRC2631, targeted gene disruptions were performed with respect to three *S. typhimurium* genes: aroA, rfaH, and thyA. The method of disruption used with respect to each gene is detailed below, although it is contemplated that any suitable method of gene disruption may be used without departing from the spirit or scope of the present invention. For purposes of this document, the term 'disruption' may include, but is not limited to, deletion of the gene in question.

Disruption of aroA

The aroA gene of *S. typhimurium* is involved in the synthetic pathways relating to aromatic amino acids as well as folic acid. Thus, disruption of the aroA gene renders the bacterium auxotrophic for aromatic amino acids. Disruption of aroA was accomplished by use of the high-transducing phage P22HT. P22HT transduction was used to insert a Tn10 cassette, a contiguous block of genes derived from the bacterial transposon Tn10, into the aroA gene, thereby disrupting the functionality thereof. The Tn10 cassette is known in the art, as it is use in disrupting bacterial genes.

Disruption of rfaH

The rfaH gene of *S. typhimurium* is involved in lipopolysaccharide (LPS) synthesis. The gene product is a transcriptional promoter that stimulates the production of LPS biosynthesis gene products. Disruption of rfaH resulted in shorter and less lipopolysaccharide production by the bacterium. The gene was disrupted via the lambda red recombination protocol, which is known in the art and provides for efficient recombination between homologous sequences as short as forty base pairs. The use of the lambda red recombination protocol in this instance resulted in deletion of the gene.

The primers used for constructing the Lambda Red recombination deletions in the rfaH gene are provided in Table 1, below, as SEQ ID NO 3 and SEQ ID NO 4. Sequences are provided in 5' to 3' orientation.

TABLE 1

Primers used for constructing Lambda Red recombination deletions in rfaH

SEQ ID NO 3: CTA AAT CTT GCG AAA ACC GGT GTT TTT TAC GCT CTG CTT GTG TAG GCT GGA GCT GCT TC

SEQ ID NO 4: ATG CAA TCC TGG TAT TTA CTG TAC TGC AAA CGC GGG CAA CAT ATG AAT ATC CTC CTT AG

Disruption of thyA

The thyA gene of *S. typhimurium* encodes thymidylate synthase A, an enzyme involved in the production of nucleic acid precursors. The disruption of thyA was also accomplished via the lambda red recombination protocol and resulted in deletion of the gene.

The primers used for constructing the Lambda Red recombination deletions in the thyA gene are provided in Table 2, below, as SEQ ID NO 1 and SEQ ID NO 2. Sequences are provided in 5' to 3' orientation.

TABLE 2

Primers used for constructing Lambda Red
recombination deletions in thyA

SEQ ID NO 1: TTA GAT AGC GAC CGG CGC TTT AAT ACC GGG GTG CGG ATC GTG TAG GCT GGA GCT GCT TC

SEQ ID NO 2: ATG AAA CAG TAT TTA GAA CTG ATG CAA AAA GTG CTG GAT CAT ATG AAT ATC CTC CTT AG

Example 1

CRC1674 Retains the Ability to Target Prostate and Breast Cancer Cells In Vivo

Figure 3:
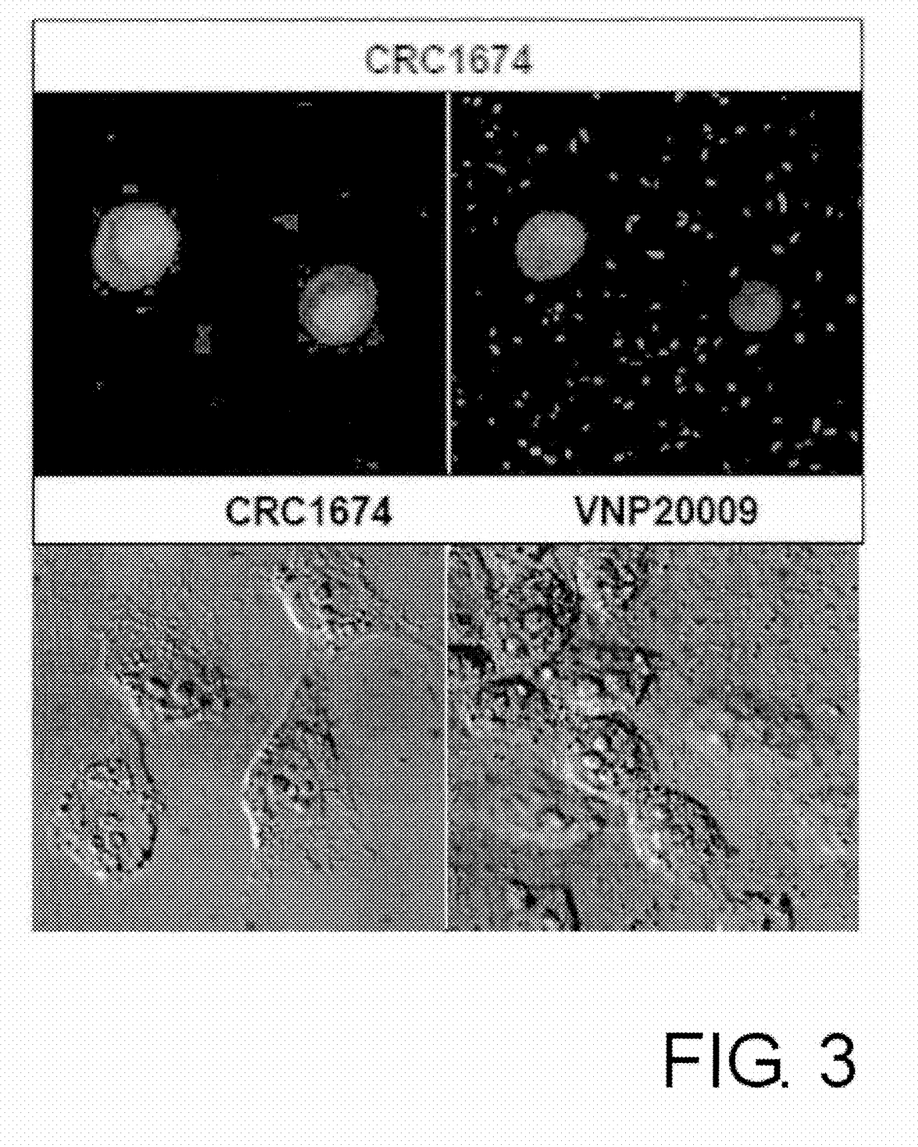
FIG. 3: Archived *S. typhimurium* preferentially targets PC-3M prostate carcinoma cells but do not target normal RWPE-1 prostate cells.

CRC1674, one of the archival LT2 strains of *S. typhimurium*, retains the ability to target prostate and breast cancer cells in vivo, as shown in FIG. 3. The top panel of FIG. 3 shows co-incubation for one hour of live RWPE-1 cells and CRC1674. Both RWPE-1 cells and CRC1674 cells were fluorescently labeled. As shown in the figure, CRC1674 showed no affinity for RWPE-1 cells. The photographs provided in the figure were obtained using confocal microscopy of two different focal planes.

The bottom panel of FIG. 3 compares the targeting of fixed PC-3M prostate cancer cells by *S. typhimurium* strains CRC1674 and VNP20009. VNP20009 is a strain of *S. typhimurium* already known to shrink solid tumors. As shown in the figure, CRC1674 more effectively targeted PC-3M than did VNP20009. A greater proportion of CRC1674 bacteria are seen attached to the PC-3M cells as compared to VNP20009, which is present in equal proportion in both cell and non-cell areas.

Example 2

CRC2631 Preferentially Invades PC-3M Cancer Cells

*S. typhimurium* strain CRC2631 was observed to attach to RWPE-1 normal prostate cells at low levels. Gentamycin exclusion assays were performed in order to determine the rate of normal RWPE-1 cell invasion versus cancer PC-3M cell invasion. An initial 2 mL of media containing about $5 \times 10^6$ to $1 \times 10^7$ colony-forming units (CFU) of *S. typhimurium* CRC2631 in co-incubation with PC-3M and RWPE-1 cells was removed after 0.5 hours of incubation and replaced with appropriate cell culture media containing 40 μg/mL gentamycin. This killed all non-invaded *Salmonella*.

Approximately 1% to 10% of the initial CRC2631 load was able to successfully invade PC-3M prostate cancer cells after a thirty-minute incubation. Less than about 0.1% to 1% of the initial CRC2631 load was able to invade the normal RWPE-1 cells over the same time period. After twenty-four hours both strains CRC1674 and CRC2631 exhibited an increase in PC-3M cells, but not in RWPE-1 cells, indicating that these strains were successfully growing in the prostate cancer cell line, but were not able to persist as effectively in the normal RWPE-1 cell line.

Example 3

Figure 1:
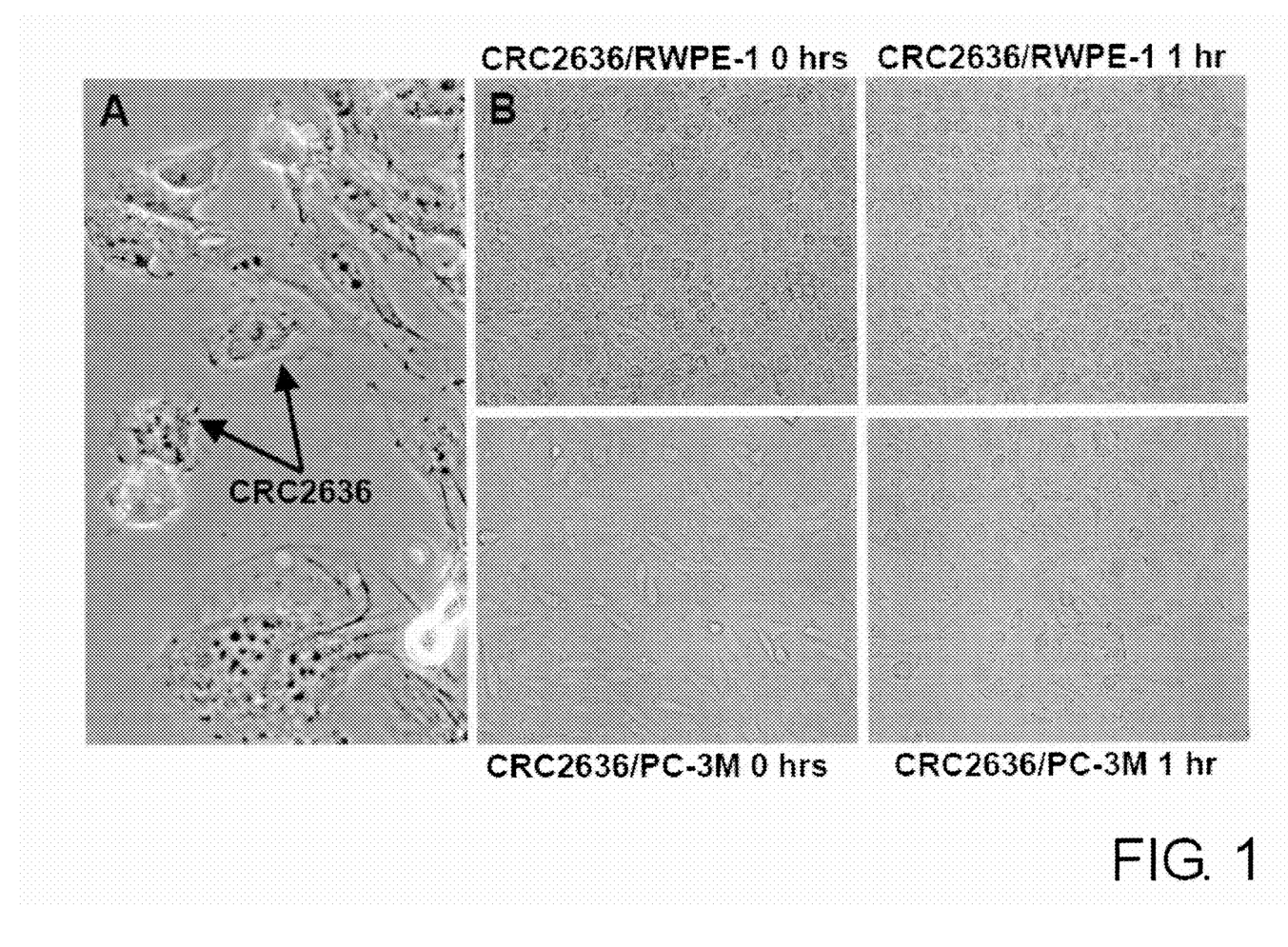
FIG. 1: Fluorescent CRC2636 binds preferentially to PC-3M cells but not to normal RWPE-1 cells.

Fluorescent CRC2636 Binds Preferentially to PC-3M Cells but not to Normal RWPE-1 Cells Strain CRC2631 was provided with a plasmid expressing a red fluorescent protein (pRST-mCherry) in order to produce fluorescent strain CRC2636. This strain was then co-incubated with RWPE-1 cells in one instance, and with PC-3M cells in a second instance. FIG. 1a shows preferential binding of CRC2626 to PC-3M after twenty minute incubation period. FIG. 1b, top panel, shows that CRC2636 did not target normal RPWE-1 cells after one hour of incubation. Conversely, FIG. 1b, bottom panel, shows that CRC2636 did in fact target PC-3M carcinoma cells after incubation for the same amount of time. As can be seen in the figure, a larger number of CRC2636 (greater than one-hundred) cells are bound to sub-confluent PC-3M cells as compared to CRC2636 cells bound to fully confluent RPWE-1 cells (approximately eight).

Example 4

CRC2631 More Effectively Invades PC-3M Carcinoma Cells Over Time

Figure 2:
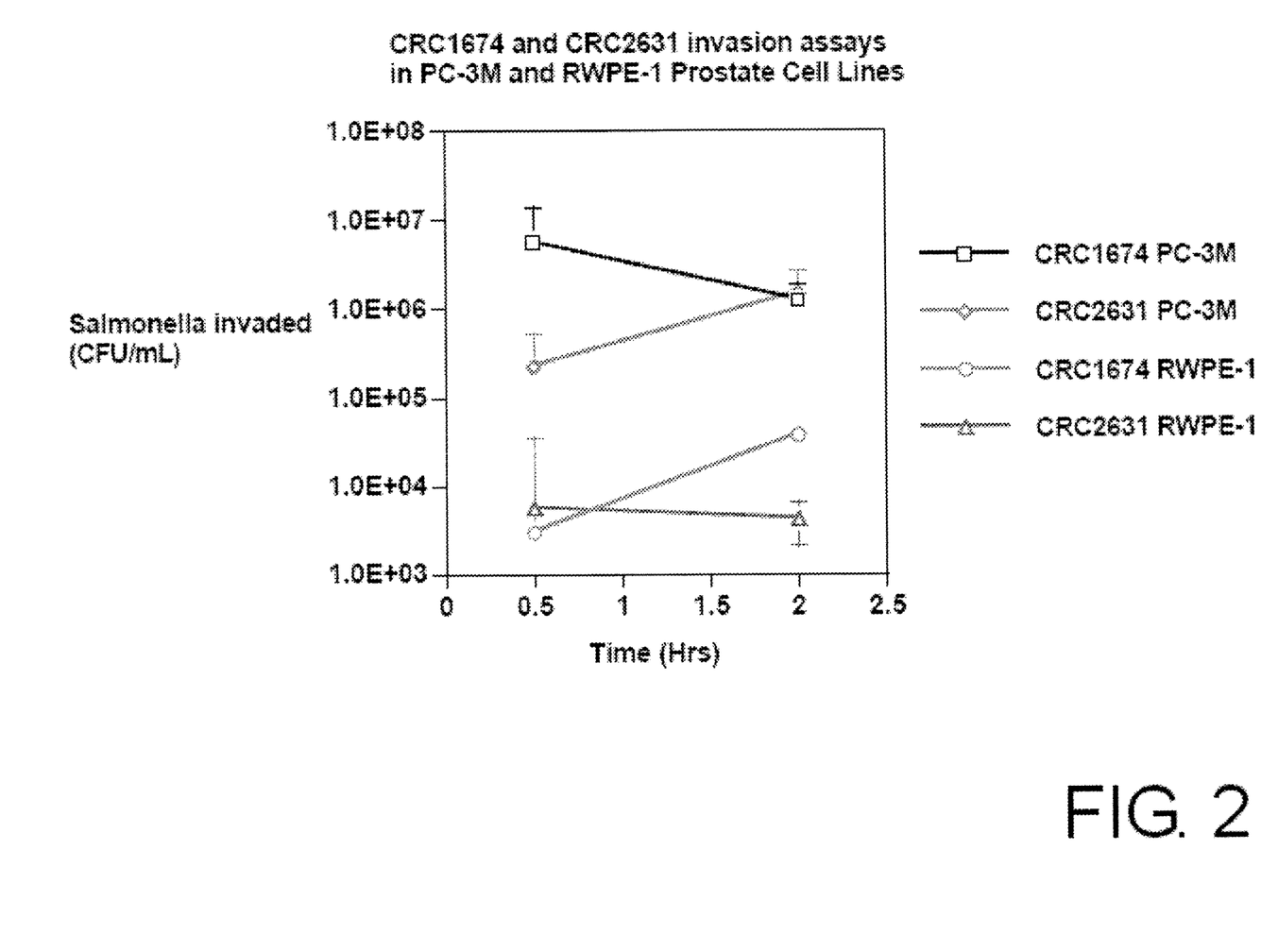
FIG. 2: CRC2631 more effectively invades PC-3M carcinoma cells over time.

Bacterial strains CRC1674 and CRC2631 were incubated with PC-3M or RPWE-1 cells for one-half hour or for two hours. Bacteria outside of cells were killed with gentamycin, and viable bacteria were recovered from within cells. FIG. 2 depicts the results, showing the number of *Salmonella* that invaded the two cell lines at either one-half or two hours. As can be seen from the figure, CRC1674 and CRC2631 cells preferentially invaded PC-3M cancer cells as compared to RWPE-1 normal cells. The ratio between the two varied from 250:1 to 1000:1.

Example 5

Figure 4:
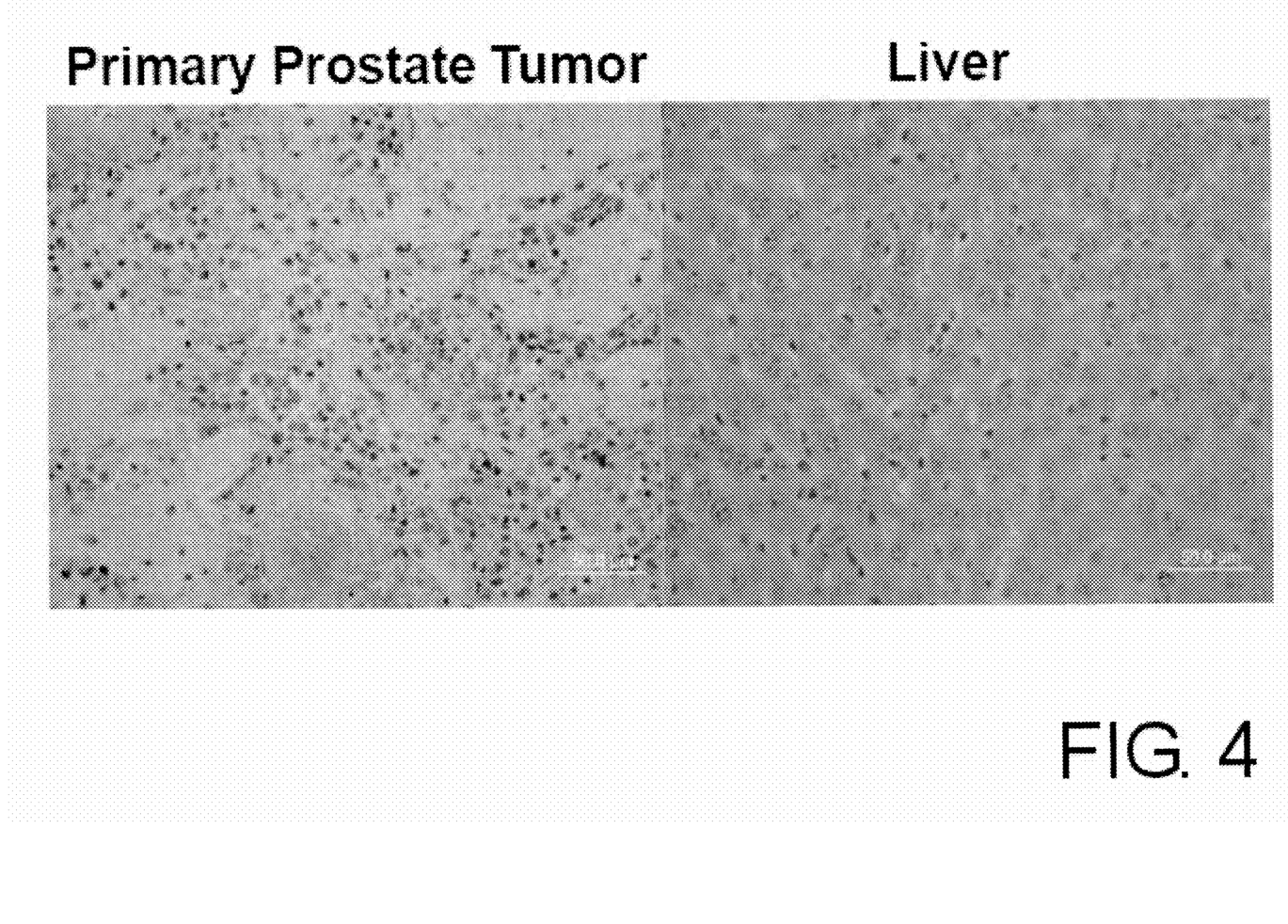
FIG. 4: Histological analysis of *S. typhimurium* CRC2636 specific targeting of primary prostate tumor.

Histological Analysis of *S. typhimurium* CRC2636 Specific Targeting of Primary Prostate Tumor CRC2636 was introduced into TRAMP mice via intra-peritoneal injection. Three days after injection, the mice were killed and primary prostate tumor and liver samples were taken and prepared for histological examination. Transmission and fluorescent photomicrographs of the same field were taken of both liver and primary prostate tumor tissue. The fluorescent field was then overlaid with the transmission photograph. The results are shown in FIG. 4. As can be seen from the figure, in vivo the fluorescent CDC2636 strain preferentially targets primary mouse prostate tumors.

Example 6

Figure 5:
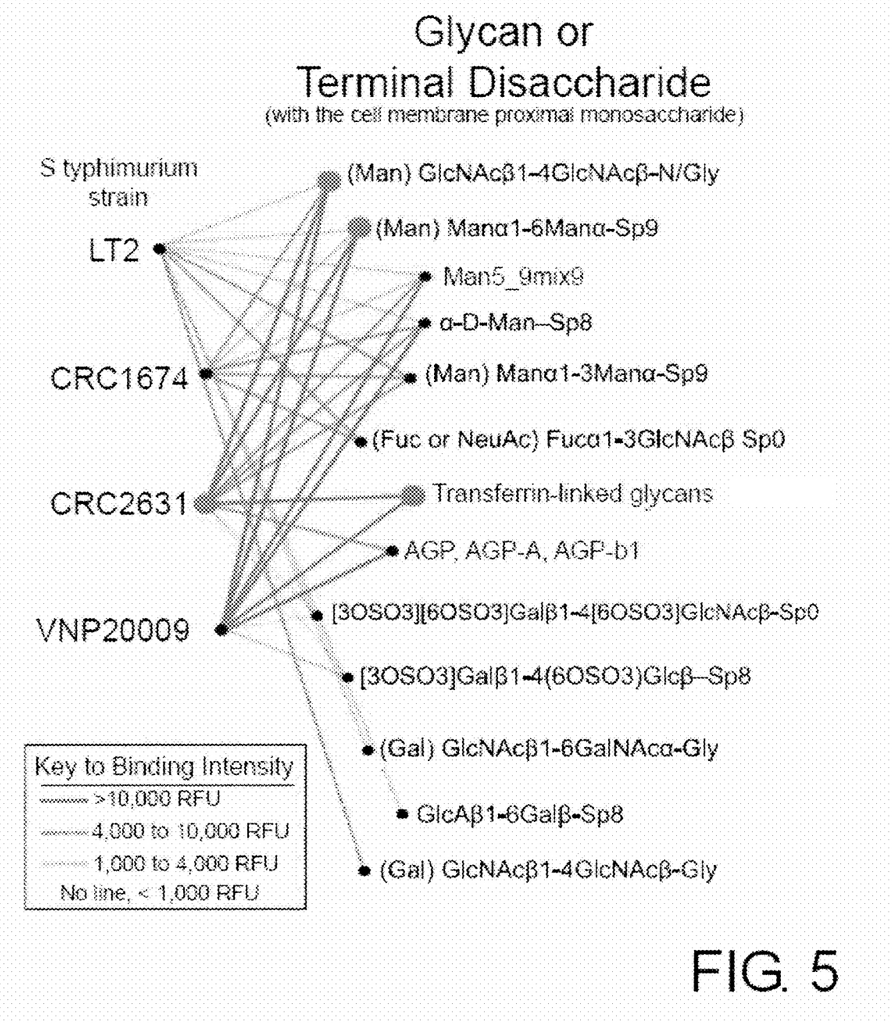
FIG. 5: CRC2631 *S. typhimurium* binds specifically to glycans present on carcinoma cells and viral proteins.

CRC2631 *S. typhimurium* Binds Specifically to Glycans Present on Carcinoma Cells and Viral Proteins Two-hundred and eighty-five eukaryotic cell glycans were extracted, purified, and spotted onto glass slides. The slides were then incubated with FITC-labeled bacteria strains LT2, CRC1674, CRC2631, and VNP20009. Binding was detected as relative fluorescence units. Six replicates were performed for each of the glycans, with the top and bottom values eliminated from each replicate. Relative fluorescence was calculated using the middle values. The results are shown in FIG. 5, in which bacterial strains are connected by lines to the glycans to which they bound, with intensity of binding indicated by the lightness or darkness of the lines. Glycans bound with high intensity by CRC2631 are indicated with large red circles.

Only CRC2631 and VNP20009 showed high intensity binding to glycans. CRC2631 bound to mannose-linked GlcNAcβ1-4GlcNAcβ-N/Gly terminal disaccharides, Manα1-3(Manα1-6)Manα-Sp9, and transferrin-linked glycans. The range of glycans to which CRC2631 binds with high intensity is reduced as compared to VNP20009, which suggests that CRC2631 binds with higher specificity to carcinoma-associated antigens. This finding can provide the basis for therapies directed to cells expressing these carcinoma-associated antigens. Expression of GlcNAcβ1-4GlcNAcβ-N/Gly terminal disaccharides is upregulated on various carcinoma cells. Carcinoma cells also express transferrin, which may play a role in carcinoma cell survival. High-mannose carbohydrates are found on viral proteins and serve as a ligand for DC-SIGN (Dendritic Cell-Specific Intercellular adhesion molecule-3-Grabbing Non-integrin).

Example 7

Microarray Characterization of CRC1674 and CRC2631 as Compared to LT2

CRC1674 (the parent strain of CRC2631, exhibiting unacceptable toxicity), CRC2631, and LT2 were each genetically profiled to determine the differences between the three strains. Because CRC1674 was derived from LT2, and CRC2631, the strain of the present invention, was developed in an attempt to create a therapeutic strain, it was desirable to determine the extent of the differences between the three. Both the CRC1674 and CRC2631 strains were profiled by generating Cy3-dCTP-labeled PCR products using random primers, then comparing their hybridization on multi-serovar *S. enterica* microarrays with the hybridization of a sequence LT2 isolate.

The majority of the CRC1674 cells were observed to have lost or have substantial changes in ten genes as compared to the sequences LT2 strain. The genes lost include the transcriptional regulator KdgR, a member of the IciR transcriptional regulator family. KdgR normally regulates pectin degradation in *Erwinia chrysanthemia* and is conserved in the Enterobacteriaceae family. Other lost or modified genes included rrmA, which encodes a rRNA guanine-N1-methyltransferase protein, a penicillin-binding protein, and six uncharacterized proteins with putative functions. Higher microarray signals in the query strain compared to LT2 indicated that the Gifsy-1 and Gifsy-2 phage genomes were amplified at positions STM1005-STM10056 and STM2584-STM2636. this indicates the existence of more copies of the Gifsy phase in CRC1674, possibly due to phage propagation or duplication.

The CRC2631 strain retained the STM1834-1843 deletions of CRC1674, and results confirmed the engineered loss of thyA and rfaH using the Red-mediated recombination protocol previously referenced. Gene amplifications in CRC2631 were distinct from those of CRC1674. In CRC2631, only the gene region from STM943-STM1013 and the Gifsy-1 phage gene STM2630 were amplified.

Figure 6:
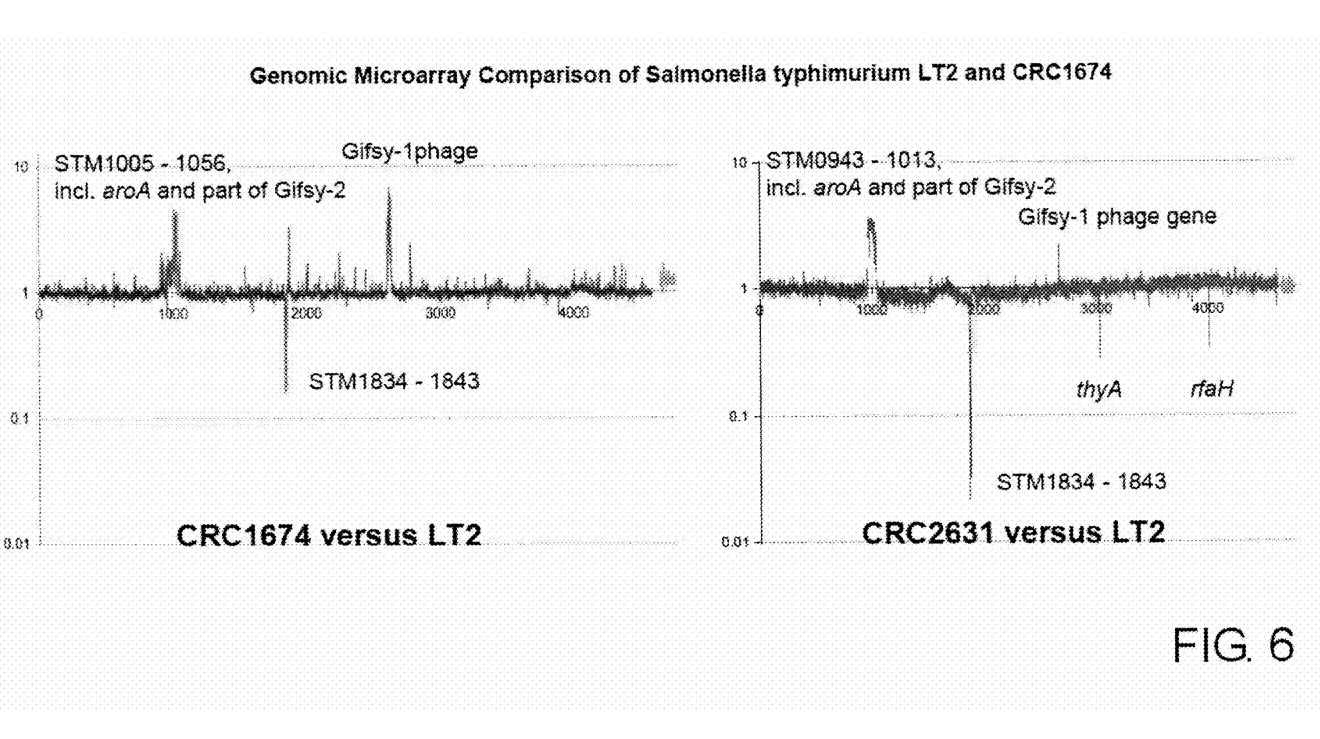
FIG. 6: DNA-DNA microarray of labeled CRC1674 and CRC2631 sequences on an LT2 gene microarray.

FIG. 6 provides the results of a DNA-DNA microarray of labeled CRC1674 and CRC2631 on an LT2 gene microarray. Gene deletions and amplifications were detected by comparing the relative fluorescence of labeled *S. typhimurium* LT2, CRC1674, and CRC2631 chromosomal DNA. Signals greater than 4600 represent genes in the pLST *Salmonella* plasmid.

Example 8

Injection Procedure in Tumor-Bearing Mammalian Models

The following procedure was generally used for injection of the therapeutic strain CRC2631 of the present invention into mice for monitoring the efficacy and toxicity of the present invention.

Overnight cultures of CRC2631 containing the pRTSm-Cherry plasmid were grown in 100 mL of LB broth with 200 µg/mL of thymine. The culture was centrifuged at 2700×g, the supernatant carefully removed, and the pellet of cells resuspended with gently shaking in 2 mL of 1×PBS. 1 mL of the cells was then diluted in PBS to a final optical density of 0.200, which represents approximately $1.0 \times 10^7$ CRC2631 bacteria/mL. Each of four mice were injected interperitoneally with 1.0 mL of each serial dilution concentration of CRC2631. The mice were monitored for toxic symptoms hourly for the first twelve hours, and then three times daily afterward.

Example 9

Toxicity Studies of CRC2631 in TRAMP Mice

Male TRAMP mice between the ages of eight and twelve weeks were injected interperitoneally (IP) with 0.9 mL of overnight CRC2631 cultures washed in PBS and diluted serially to determine the minimum toxic dose in the mammalian mouse model. The IP injections were performed according to the following procedure:

To prepare an overnight culture for injection, frozen stock was streaked onto LB agar with 200 µg/mL thymine. The plates were incubated overnight at 37 degrees C. A 25 mL culture of CRC2631 in LB broth having 200 µg/mL thymine added thereto was started from a single isolated colony from one of the agar plates. The culture was incubated in a shaking 37° C. water bath overnight. The following day, the 25 mL culture was spun down at 4000 rpm for ten minutes in a 50 mL conical tube using a swing bucket rotor. The supernatant was discarded and the pellet of cells resuspended in 25 mL 1×PBS. The optical density of the therapeutic strain was normalized to Abs 600=0.200 and the culture was transported to the facility housing the TRAMP mice.

For each mouse to be injected, 0.9 mL of the *Salmonella* test culture was drawn into a sterile hypodermic syringe. The injection site on each mouse was sterilized with 70% ethanol and the interperitoneal injection was made. The mice were checked at four, eight, and twelve hours post-injection.

Male TRAMP mice were selected because of their tendency to spontaneously develop primary and secondary prostate cancer cells after twenty weeks of age. The mice tolerated single injections of up to about $2 \times 10^8$ CFU of CRC2636 bacteria. When the therapeutic bacteria were injected into mice having prostate tumors, the tumors were found to have *Salmonella* loads two-fold to one-hundred-fold higher than the liver after two to three days.

Example 10

Tolerance of *S. typhimurium* strain CRC2636 Injected into TRAMP Mice with and without Primary Tumors Table 3, below, provides the results of injection of strain CRC2636 into TRAMP mice both with and without primary tumors. Injections were performed intraperitoneally with strain CRC2636 cells suspended in PBS. The column labeled 'deaths' refers to mice that either died or were rapidly crashing (i.e. dying) before sacrifice. 'Survival' is an indication of how long, in days, mice survived before sacrifice. Non-tumor bearing mice were co-injected with tumor-bearing mice in order to compare survival rates. None of these mice suffered ill effects from any of the CRC2636 injections. Mice living for 2-3 days were sacrificed intentionally to determine the location and number of *Salmonella* in the mouse model (the prostate tumor, liver, and spleen).

TABLE 3

| TRAMP Mice | Number of Mice | CRC2636 Dose (CFU/IP Injection) | Deaths (total number treated) | Mean Survival (Days) | Median Survival (Days) | Range of Survival (Days) |
|---|---|---|---|---|---|---|
| Tumor-bearing, injected | 22 | $9.3e^4$ to $3.3e^7$ | 9/22 | 2.2 | 2 | 1 to 14 |
| Non-tumor bearing, injected | 4 | $5.9e^6$ to $3.3e^7$ | 0(4) | 2.8 | 3 | 2 to 3 |
| Non-tumor bearing, injected | 4 | $1.18e^8$ | 1(4) | 398 | 525+ | 18 to 525+ |
| Non-tumor bearing, injected | 4 | $1.24e^7$ | 0(4) | 525+ | 525+ | 525+ |

FURTHER ASPECTS OF THE INVENTION

One of skill in the art will recognize further aspects of the present invention based on the disclosure provided herein. For example, it is contemplated that the *Salmonella* of the present invention could be associated with a therapeutic agent effective against cancer and the *Salmonella* used to target cancer cells for delivery of the therapeutic agent. It is further contemplated that a therapeutic agent effective against cancer could be bound to a molecule targeting the glycans described above as specifically bound by *S. typhimurium* strain CRC2631, thereby delivering the therapeutic agent to cells having those specific glycans expressed on a membrane thereof.

The detailed description set forth above is provided to aid those skilled in the art in practicing the present invention. The invention described and claimed herein, however, is not to be limited in scope by the specific embodiments disclosed because these embodiments are intended to be illustrative of several aspects of the invention. Any equivalent embodiments are intended to be within the scope of the present invention. Various modifications of the invention that do not depart from the spirit or scope of the present invention, in addition to those shown and described herein, will become apparent to those skilled in the art from the foregoing description. Such modifications are also intended to fall within the scope of the appended claims.

Having thus described the preferred embodiment of the invention, what is claimed as new and desired to be protected by Letters Patent includes the following:

---

The invention claimed is:

1. A biologically pure isolate of the genus *Salmonella* comprising archival strain CRC1674, wherein the isolate further comprises a disruption of at least one gene selected from the group consisting of aroA, rfaH, and thyA.

2. The biologically pure isolate of the genus *Salmonella* according to claim 1, comprising a disruption of each of the genes aroA, rfaH, and thyA.

3. The biologically pure isolate of the genus *Salmonella* according to claim 2, wherein the biologically pure isolate comprises *Salmonella typhimurium* strain CRC2631.

4. The biologically pure isolate of the genus *Salmonella* according to claim 3, wherein the biologically pure isolate consists of *Salmonella typhimurium* strain CRC2631.

* * * * *